United States Patent [19]

Holtkamp

[11] Plant 4,776

[45] Oct. 13, 1981

[54] AFRICAN VIOLET PLANT

[76] Inventor: Reinhold Holtkamp, Werther Strasse 112, D-4294 Isselburg, Fed. Rep. of Germany

[21] Appl. No.: 172,395

[22] Filed: Jul. 25, 1980

[51] Int. Cl.[3] ..... A01H 5/00
[52] U.S. Cl. ..... Plt./69
[58] Field of Search ..... Plt./69

*Primary Examiner*—Robert E. Bagwill
*Attorney, Agent, or Firm*—Schwartz, Jeffery, Schwaab, Mack, Blumenthal & Koch

[57] ABSTRACT

An African violet named Texas, particularly characterized by its vigorous and very uniform growth habit, dark green, shiny leaves, upright stems each of which carries 7–12 flowers, and by its large blue frilled flowers which are long lasting and non-dropping.

1 Drawing Figure

1

The present invention comprises a new and distinct cultivar of African violet plant, botanically known as *Saintpaulia ionantha,* and hereinafter referred to by the cultivar name Texas.

The new cultivar was referred to during the breeding and selection process by the designation D102/2, and is a product of a planned breeding program. The basic objective of the breeding program was to create a new African violet cultivar having relatively large blue frilled blossoms.

The new cultivar was originated from a cross made in a controlled breeding program in Isselburg, West Germany. The female, or seed parent was a cultivar designated b. 36/1, blue frilled. The male, or pollen parent was Wisconsin, disclosed in my U.S. Plant Pat. No. 4,353.

The new cultivar Texas was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and are retained through successive generations of asexual reproduction.

Texas has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Texas, which in combination distinguish this African violet as a new and distinct cultivar:

1. Vigorous and very uniform growth habit.
2. Upright, wire-like stems, approximately 9 in number, each of which carries 7–12 flowers.
3. Large blossoms, blue in color and having frilled edges.
4. Flexible petioles.
5. Relatively dark green leaves.
6. Attractive saleable plant with compact and rich flower head within 10 weeks after potting.

2

The new cultivar is distinguished from Wisconsin by its more vigorous growth, frilled flowers, more profuse flowering, and by its large flower diameter.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. v. Texas.

Parentage:

*Male parent.*—Wisconsin (U.S. Plant Pat. No. 4,353).

*Female parent.*—b. 36/1, blue frilled.

Propagation: The new cultivar holds its distinguishing characteristics through successive propagations by leaf cuttings.

Plant: From 8 cm. to 11 cm. tall when grown in pots, and approximately 25–30 cm. in diameter when fully grown.

Leaves:

*General form.*—Oval.

*Diameter.*—Up to 65–75 mm.

*Texture.*—Soft, hairy.

*Aspect.*—Velvety, very shiny.

*Veins.*—Upperside visible; underside well-pronounced and shiny; on younger leaves underside brownish-purple and hairy.

*Color (upperside).*—HCC Parsley green 00962.

*Color (underside).*—HCC Willow green 000862/3, with purplish shade.

*Petiole.*—Purplish brown, hairy.

Flowers:

*Buds.*—Ball-shaped; 7–9 mm. just before opening, 7–12 per stem.

*Sepals.*—Color: Greenish brown. Calyx: Flat, funnel-shaped. Aspect: Spear-shaped but wider than normal. Peduncle: Short, wire-like, dark brown, hairy.

Individual flowers:

*Size.*—Between 45–55 mm.

*Color.*—Upperside: Moorish blue 739/2. Underside: Dauphin is violet 039/1.

*Borne.*—7–12 large frilled flowers; frilled edges seem darker on underside; flowers display an additional small petal in the center of the flower.

*Shape.*—Conventional violet shape; 2 small petals, 3 large petals, with an additional small petal in center.

*Flowering time.*—6–7 weeks after potting first flowers appear; 8–10 weeks to full-flowering saleable plant.

Reproductive organs:

*Anthers.*—2, composed of 4 cells, with seed capsule pushed slightly through; color Sulphur yellow/1.

*Filaments.*—3–4 mm. long, light yellowish-green; purple stripe on side.

*Styles.*—7 mm., campanula violet 37; base of ovary light green, hairy.

*Pollen color.*—HCC 64/3 Dresden yellow.

Roots: White, velvety, normally developed.

Disease resistance: Good as experienced to date.

General observations: Texas is a very vigorous grower with dark green, velvety, very shiny leaves. There are often 7–12 or more flower stems each of which carries up to 15 long-lasting large frilled and blue non-dropping flowers.

I claim:

1. A new and distinct cultivar of African violet known by the cultivar name Texas, as described and illustrated, and particularly characterized by its vigorous and very uniform growth habit, dark green, shiny leaves, upright stems each of which carries 7–12 flowers, and by its large blue frilled flowers which are long lasting and non-dropping.

* * * * *

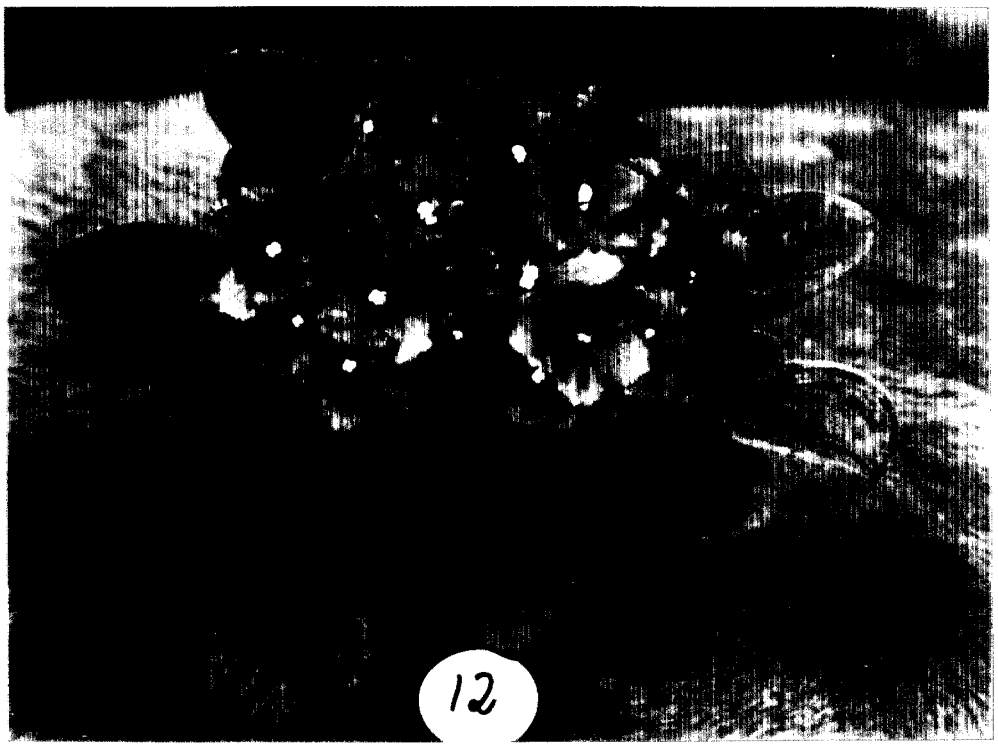
12